United States Patent [19]

Billenstein et al.

[11] 4,167,639
[45] Sep. 11, 1979

[54] FLUORINATED SULFOSUCCINATES

[75] Inventors: Seigfried Billenstein, Burgkirchen; Heinz Brecht, Bad Soden; Dieter Hoffmann, Bobingen, all of Fed. Rep. of Germany

[73] Assignee: Hoechst Aktiengesellschaft, Frankfurt am Main, Fed. Rep. of Germany

[21] Appl. No.: 878,881

[22] Filed: Feb. 17, 1978

Related U.S. Application Data

[63] Continuation of Ser. No. 657,549, Feb. 12, 1976, abandoned, which is a continuation of Ser. No. 477,321, Jun. 6, 1974, abandoned.

[30] Foreign Application Priority Data

Jun. 9, 1973 [DE] Fed. Rep. of Germany ....... 2329660

[51] Int. Cl.$^2$ ............................................... C09G 1/08
[52] U.S. Cl. .................................... 560/151; 106/10; 106/271; 252/353; 252/355
[58] Field of Search ........................ 106/10, 270, 271; 252/311, 353, 532, 355; 560/151

[56] References Cited

U.S. PATENT DOCUMENTS 3,137,713  6/1964  Shen et al. ........................ 260/400

Primary Examiner—Lorenzo B. Hayes
Attorney, Agent, or Firm—Connolly and Hutz

[57] ABSTRACT

Addition products of water-soluble sulfites or disulfites to maleic acid mono- or diesters of partially fluorinated alkanols or the mono-, di- or triethyleneglycol ethers of these alcohols are useful as surface active agents, especially as wetting agents, as levelling agents in wax emulsions or as dispersants.

10 Claims, No Drawings

FLUORINATED SULFOSUCCINATES

This application is a continuation of application Ser. No. 657,549 filed Feb. 12, 1976 now abandoned which is a continuation of application Ser. No. 477,321 filed June 6, 1974 and now abandoned.

Addition products of sulfites on maleic acid mono- and diesters of long-chain fatty alcohols and their use as surface-active agents are already known.

It has now been found that compounds of the formula I $$RO-CO-CH_2-CH(SO_3M)-O-OR'$$

wherein M is a cation, R stands for a group of the formula II $$R_f-(CH_2)_m-OCH_2CH_2)_n$$

wherein $R_f$ stands for a straight-chain perfluoroalkyl radical or a terminally methyl-branched perfluoroalkyl radical, i.e. a perfluoroalkyl group carrying a trifluoro methyl group in the penultimate position, each group having 2 to 8 carbon atoms, m is a number of from 1 to 4 and n is a number of from 0 to 3, and R' has the meaning of R or M, are obtained when maleic acid anhydride is reacted with one or two mol equivalents of an alcohol of the formula III $$ROH$$

in which R is as defined above, wherein in the reaction with 2 mols of alcohol an acidic esterification catalyst is added, and to the maleic acid ester thus obtained a water-soluble sulfite is added in an aqueous medium in the presence of a solubilizer, and optionally subsequently the cation M is exchanged partly or completely.

The alcohols of the formula ROH are known (U.S. Pat. Nos. 2,666,797 and 3,171,861, German Offenlegungsschriften Nos. 2,028,459 and 1,468,253) and can be prepared easily. Alcohols of the formula III having 1, 2 or 4 methylene groups (m=1, 2 or 4) are preferred, since they are obtained in an industrial scale from perfluorocarboxylic acids and the derivatives thereof by hydrogenation (m=1) or from perfluoroalkyl iodides by reacting with 1 or 2 mols of ethylene and saponification of the iodide thus obtained (m=2 or 4). In the latter case the mixtures obtained in the industrial process may be used directly, as well as, of course, mixtures with other alcohols of the mentioned type (thus, m may be a fraction).

In the case of the straight-chain compounds the perfluoroalkyl radical of the alcohols ROH contains 2 to 8, preferably 4 to 6 carbon atoms and in the case of the branched radicals, 3 to 8, preferably 5 to 7 carbon atoms. Since the starting materials are often obtained by telomerization of tetrafluoroethylene on to lower perfluoroalkyl iodides mixtures of such compounds are especially interesting, that means the number of the carbon atoms is not necessarily an integer.

By known oxethylation methods the corresponding oxethylates (n=1 to 3) are prepared from the starting materials having n=0. It is known that the oxethylation products generally are mixtures having a different content of oxethyl groups (i.e. n is an average value which represents i.a. a fraction). These mixtures may be separated by distillation or chromatography; in general the mixtures are used directly since they have the same activity.

Alcohols to be reacted according to the invention of the formula III are for example $C_2F_5-CH_2-CH_2-OH$
$(CF_3)_2CF-CH_2-CH_2-O-CH_2-CH_2-OH$
$CF_3-(CF_2)_3-CH_2-OH$
$CF_3-(CF_2)_4-CH_2-(O-CH_2-CH_2)_2-OH$
$(CF_3)_2CF-CF_2-CF_2-CH_2-CH_2-(OCH_2CH_2)_3-OH$
$CF_3-(CF_2)_5-(CH_2)_3-OH$
$CF_3-(CF_2)_6-(CH_2)_4-OH$
$(CF_3)_2CF(CF_2)_5-CH_2-(O-CH_2CH_2)_2-OH$
$CF_3(CF_2)_7-(CH_2)_2-OH.$ The alcohols of the formula III are reacted in known manner (Houben-Weyl, Methoden der organischen Chemie, 3rd edition, volume 9, page 383 (1955) and K. Lindner, Tenside, Hilfsmittel Waschrohstoffe; Wissenschaftliche Verlagsgesellschaft, Stuttgart 1965, page 747) with 1 mol of maleic acid anhydride to give the maleic acid monoester (maleic acid semiester) or with half a mol of maleic acid anhydride in the presence of an acidic esterification catalyst to give the maleic acid diester. As acid esterification catalysts may be used for example borontrifluoride or mineral acids such as phosphoric acid, perchloric acid or preferably sulfuric acid.

The maleic esters thus obtained in a high purity of more than 97% and in a pratically quantitative yield, are reacted with water-soluble sulfites in an aqueous medium, with the aid of a solubilizer. As solubilizer are suitable water-soluble polar organic solvents, such as lower alcohols, for example methanol, ethanol, isopropanol; lower ketones, such as acetone; ethers, such as tetrahydrofuran or dioxan etc. Water-soluble sulfites are above all alkalimetal and ammonium sulfites and the corresponding hydrogen sulfites or disulfites. The easiest way is to react the semiesters with sulfites and the diesters with disulfites, according to the following equations:

$$ROOC-CH=CH-COOH + M_2SO_3 \rightarrow$$
$$ROOC-CH_2-\underset{SO_3M}{\underset{|}{CH}}-COOM$$

$$2\ ROOC-CH=CH-COOR + M_2S_2O_5 + H_2O \rightarrow$$
$$2\ ROOC-CH_2-\underset{SO_3M}{\underset{|}{CH}}-COOR$$

The cation M may be exchanged partly or completely by another cation by preparing from the salts obtained the free acids with mineral acid and by isolating them, if desired, and converting them, if desired, with bases into other salts. Suitable bases are above all amines which carry lower alkyl groups, which may be substituted by solubilizing groups such as hydroxy, carboxy and sulfo groups. Such amines are especially mono-, di-and triethanol amine, glycine, taurine and N-methyltaurine. Salts such as amines are especially suitable for preparing high-percentage solutions of the products of the invention.

Depending on the length of the fluoroalkyl chain, on the ethylene oxide content and on the type of the ester the products of the invention are obtained as highly viscous, colorless to slightly yellow masses or as white powders.

The products of the invention are soluble in water and have the property of strongly reducing the surface tension of water even in the case of low initial concentrations (Table 1). The very low surface tension values, combined with excellent wetting properties, open a large field of application to the compounds of the invention. Thus, these compounds are excellent wetting agents for fibre materials, which is particularly important in dyeing processes, textile finishing processes, purification and washing processes.

Further possibilities for the technical application of the compounds of the invention are their addition as levelling agents to dispersions and their addition in order to increase the wetting properties of other wetting agents, for example in the wetting of powdery materials such as silica, chalk and spray powders.

Furthermore the compounds of the invention are characterized by their excellent levelling capacity in the case of self gloss emulsions which may be used for example for the polish of the floor. The addition of these surface-active compounds brings about an excellent distribution of wax emulsions on very different surfaces, for example floor coverings, whereby, when drying, the formation of undesired stains and rims is reduced or completely avoided.

The novel compounds are obtained as solutions. These solutions may be incorporated as such into wax emulsions or the compounds are obtained free from solvents by spray drying or evaporating. By extraction with ether they may be freed, if desired, from small amounts of maleic ester or fluoroalcohol.

It is significant that also the novel compounds having a short-chain perfluoroalkyl radical are surface-active. Thus, if starting materials from a telomerization reaction are used, it is not necessary to separate the compounds having short-chain radicals, since the corresponding products of the invention do not represent a "ballast" which would be inacceptably expensive in the present case. Thus, the compounds of the invention are additionally superior to other fluoroalkyl surfactants with regard to the working up of the starting materials which is not necessary or easier.

The following Examples illustrate the invention. Percentages and parts are by weight unless specified otherwise, the ratio of parts by weight to parts by volume being that of the kilogram to the liter.

EXAMPLE 1

19.5 g of 1,1,2,2-tetrahydroperfluoro-butanol (=119 mmols), 5.8 g of maleic acid anhydride (=59.2 mmols) and 0.1 g of concentrated sulfuric acid (=0.5% calculated on fluoroalcohol) were introduced into a 100 ml flask and stirred for 16 hours under inert gas (nitrogen) at 140° C., while 0.5 ml of water (=28 mmols) was distilled off. The maleic acid diester was distilled at 0.2 torr/90° C.-188° C.

In a 250 ml flask 5.6 g of sodium disulfite (=29.5 mmols), 80 ml of water and 40 ml of isopropanol were added to the distillate (24.3 g = 59.3 mmols) and refluxed for 16 hours at 80° C. until a clear solution resulted from the two phases. Subsequently the solvent was evaporated in the vacuum drying cabinet at 50° C./12 torr. 23 g of a white product having a melting point of 269° C. (decomposition) were obtained. The yield was 95.4%.

EXAMPLE 2

50 g of 1,1,2,2-tetrahydroperfluoro-hexanol (=189 mmols) and 18.6 g of maleic acid anhydride (=190 mmols) were introduced into a 100 ml flask and stirred for 20 hours at 140° C. The acid number of the monoester was determined: AN=149 (calculated = 155). The monoester was filled into a 250 ml flask and 23.9 g of sodium sulfite (=190 mmols), 100 ml of water and 50 ml of isopropanol were added and the whole was refluxed for 8 hours at 80° C. It was boiled until a clear solution resulted from the two phases. Then the solvent was removed. 91 g of a yellow product in the form of a paste were obtained which had the following elementary analysis:

|    | Found: | Calc:  |
|----|--------|--------|
| C: | 24.8%  | 24.5%  |
| H: | 1.4%   | 1.4%   |

The yield was 98.5%.

EXAMPLE 3

171 g of 1,1,2,2-tetrahydroperfluorohexyl-glycol ether (=555 mmols) and 54.7 g of maleic acid anhydride (=555 mmols) were introduced into a 500 ml flask and stirred for 16 hours at 140° C. The acid number of the ester was determined: AN=137 (calculated 135). The monoester was filled into a 1 liter flask, and 70.5 g of sodium sulfite (=555 mmols), 400 ml of water and 200 ml of isopropanol were added and the mixture was refluxed until a clear solution resulted from the two phases. The solvent was removed. The yield was 280 g (=94% of the theory).

In the same manner 20 g of 1,1,2,2-tetrahydroperfluorohexyltriglycol ether (=50 mmols) and 5 g (=50 mmols) of maleic acid anhydride were reacted. After refluxing with sodium sulfite solution (6.5 g = 50 mmols) and removing the solvent, 26 g (=80% of the theory) of a slightly yellow-colored paste were obtained.

EXAMPLE 4

600 g of 1,1,2,2-tetrahydroperfluoro-hexanol (=2.27 mmols), 115.5 g of maleic acid anhydride (=1.14 mols) and 1.2 g of concentrated sulfuric acid (=0.2% calculated on fluoroalcohol) were introduced into a 500 ml flask and stirred for 24 hours under inert gas (nitrogen) at 140° C. while 15 ml of water (=834 mmols) were distilled off. After cooling the acid number was determined (AN=5). 107.8 g of sodium disulfite (=567 mmols), 1.0 liter of water and 500 ml of isopropanol were added to the maleic acid diester and the mixture was refluxed for 24 hours at 80° C. until a clear solution resulted from the two layers.

Subsequently the solvent was removed. The yellowish solid substance obtained was extracted with diethyl ether. 600 g of the extraction residue were obtained with the following elementary analysis:

|    | Found: | Calculated: |
|----|--------|-------------|
| C: | 26.8%  | 27.0%       |
| H: | 1.9%   | 1.55%       |

Melting point: 244° C. (decomposition)
The yield was 75%.

EXAMPLE 5

100 g of 1,1,2,2-tetrahydroperfluorohexyl-glycol ether (=308 mmols), 15.9 g of maleic acid anhydride (=162 mmols) and 0.2 g of concentrated sulfuric acid (=0.2% calculated on fluoroalcohol) were introduced into a 250 ml flask and stirred for 24 hours under inert gas (nitrogen) at 140° C., while 3 ml of water (=160 mmols) were distilled off. From time to time the acid number was determined: After 8 hours the acid number was 33.4; after 16 hours 24.03, after 24 hours it was 10.0 and after 40 hours the acid number was 4.0.

After cooling 15.4 g of sodium disulfite (=79 mmols), 300 ml of water and 150 ml of isopropanol were added to the maleic acid diester and the mixture was refluxed for 16 hours until a clear solution resulted from the two phases. Then the solvent was removed in the vacuum drying cabinet at 50° C./ 12 torr. 114 g (=89% of the theory) of a slightly yellow paste were obtained.

In similar manner 100 g (=285 mmols) of 1,1,2,2-tetrahydroperfluorohexyl-diglycol ether and 61 g (=155 mmols) of 1,1,2,2-tetrahydroperfluoroalkyl-triglycol ether were reacted with maleic acid anhydride and then with sodium disulfite. 112 g (=89% of the theory) and 60 g (=80% of the theory), respectially, of slightly yellow pastes were obtained.

EXAMPLE 6

50 g of 1,1,2,2-tetrahydroperfluoro-octanol (=137 mmols) and 13.5 g of maleic acid anhydride (=137 mmols) were introduced into a 250 ml flask and stirred for 16 hours at 140° C. The acid number of the ester was determined: AN=110.2 (calc. 121). 17.3 g of sodium sulfite (=137 mmols), 100 ml of water and 50 ml of isopropanol were added to the ester, the mixture was refluxed for 16 hours until a clear solution was obtained and then the solvent was removed. 77 g of a white product (=95.5% of the theory) were obtained with the following elementary analysis:

|   | Found: | Calculated: |
|---|--------|-------------|
| C: | 23.4% | 24.5% |
| H: | 1.7% | 1.2% |

EXAMPLE 7

40 g of 1,1,2,2-tetrahydroperfluoro-diglycol ether (=88.4 mmols) and 8.7 g of maleic acid anhydride (=88.4 mmols) were introduced into a 250 ml flask and stirred for 24 hours at 140° C. The ester was introduced into a 500 ml flask and mixed with 11.2 g of sodium sulfite (=88.6 mmols), 200 ml of water and 100 ml of isopropanol and refluxed for 24 hours at 80° C., until a clear solution was obtained from the two phases. The solvent was removed. 56 g of the product (=93.5% of the theory) were obtained.

EXAMPLE 8

600 g of 1,1,2,2-tetrahydroperfluoro-octanol (=1.65 mols), 80.8 g of maleic acid anhydride (=0.8 mol) and 1.0 g of concentrated sulfuric acid (=0.2% calculated on fluoro-alcohol) were introduced into a 500 ml flask and stirred for 16 hours under inert gas (nitrogen) at 140° C., whereby 14 ml of water (=0.8 mol) were distilled off. The acid number of the ester was determined: AN=5.5, 65.7 g of sodium disulfite (345 mmols), 1.0 l of water and 0.5 l of isopropanol were added to the maleic acid diester and refluxed for 20 hours at 80° C., until a clear solution resulted from the two phases; then the solvent was evaporated. 628 g (=86% of the theory) of the product were obtained with the following elementary analysis:

|   | Found: | Calculated: |
|---|--------|-------------|
| C: | 26.8% | 26.3% |
| H: | 1.4% | 1.2% |

Melting point: 252° C.

EXAMPLE 9

66.5 g of 1,1,2,2-tetrahydroperfluorooctyl-diglycol ether (=147 mmols), 7.2 g of maleic acid anhydride (=73.5 mmols) and 0.1 g of concentrated sulfuric acid (=0.2% calculated on fluoro-alcohol) were introduced into a 250 ml flask and stirred for 20 hours under inert gas (nitrogen) at 140° C.; thereby 1 ml of water (=55 mmols) were distilled off. The acid number of the ester was determined: AN=6.5. 7.1 g of sodium disulfite (=37.5 mmols), 150 ml of water and 75 ml of isopropanol were added to the maleic acid diester and the mixture was refluxed for 14 hours at 80° C. until a clear solution resulted from the two phases. Then the solvent was removed. 72 g of the product (=90.5% of the theory) were obtained.

EXAMPLE 10

200 g of 1,1,2,2-tetrahydroperfluoro-decanol (=431 mmols) and 42.6 g of maleic acid anhydride (=434 mmols) were introduced into a 500 ml flask and stirred for 20 hours at 140° C. The acid number of the ester was determined: AN=83.8 (calculated: 100). 55.2 g of sodium sulfite (438 mmols), 400 ml of water and 200 ml of isopropanol were added to the reaction product, the whole was refluxed until a clear solution was obtained. The solvent was removed. 257 g of the product (=86.5% of the theory) were obtained.

Melting point: >300° C.

EXAMPLE 11

100 g of 1,1,2,2-tetrahydroperfluoro-decanol (=216 mmols), 10.6 g of maleic acid anhydride (=108 mmols) and 0.2 g of concentrated sulfuric acid (=0.2% calculated on fluoroalcohol) were introduced into a 250 ml flask and stirred for 24 hours under inert gas and at 140° C.; 1 ml (=55 mmols) of water was distilled off. The acid number of the ester was determined (AN=7.0). 10.3 g of sodium disulfite (=54.2 mmols), 300 ml of water and 150 ml of isopropanol were added to the maleic acid diester, and the mixture was refluxed for 24 hours at 80° C. until a clear solution was obtained from the two phases. Then the water/isopropanol mixture was removed. 106 g of the product (=89% of the theory) were obtained.

Melting point: 186° C.

EXAMPLE 12

1304 g of 1,1,2,2-tetrahydroperfluoro-octanol (=3.6 mols), 326 g of 1,1,2,2-tetrahydroperfluoro-hexanol (=1.3 mols) and 461.7 g of maleic acid anhydride (=4.7 mols) were introduced into a 2 l flask and stirred for 22 hours at 140° C. The acid number of the ester was determined: AN=139 (calculated 127). 594 g of sodium sulfite (4.7 mols), 2.2 l of water and 1.1 l of isopropanol were added to the ester and the mixture was refluxed for 16 hours at 80° C. until a clear solution resulted. The solvent was removed. 1954 g of the product (=73% of the theory) were obtained

EXAMPLE 13

1600 g of 1,1,2,2-tetrahydroperfluoro-octanol (=4.4 mols), 400 g of 1,1,2,2-tetrahydroperfluoro-octanol (=1.5 mols), 284 g of maleic acid anhydride (2.9 mols) and 4.5 g of concentrated sulfuric acid (0.2% calculated on fluoro-alcohol) were introduced into a 2 l flask and stirred for 22 hours under inert gas (nitrogen) at 140° C., while 34 ml of water (=1.9 mols) were distilled off (acid number 6.0). 275.3 g of sodium disulfite (=1.45 mols), 1.8 l of water and 0.9 l of isopropanol were added to the ester and refluxed for 16 hours at 80° C. until a clear solution was obtained. The solvent was removed. 2130 g of the product (=84.4% of the theory) were obtained.

EXAMPLE 14

To a wax emulsion basic preparation consisting of a montan wax having a dropping point of 83° to 89° C., an acid number of 85 to 95 and a saponification number of 120 to 145 (15 parts), of diethanol amine (3.0 parts) and water (82.0 parts), the substances to be examined were added in such amounts as to obtain a concentration of fluorine of 0.02 to 0.05%. The surface tension values of these test emulsions were measured.

If 0.13 ml of the wax emulsions which contained 0.025 part of fluoro surfactant was applied onto a purified polyvinylchloride (PVC) plate having a size of 7×10 cm, the distribution and spreading capacity were the better, and after drying the formation of staine and rims was the smaller (visual estimination), the lower the surface tension value of the emulsions used was (see Table 2).

EXAMPLE 15

To a wax emulsion basic preparation consisting of a polyethylene wax having a dropping point of 97° to 102° C., an acid number of 14 to 18 and a saponification number of 20 to 35 (12 parts), of oleic acid (1.6 parts), diethylamino ethanol (1.6 parts) and water (84.6 parts), the substances were added in such amounts as to obtain a concentration of fluorine of 0.02 or 0.05%. The surface tension values of these test emulsions were measured.

If 0.15 ml of the wax emulsions which contained 0.025 part of fluoro-surfactant was applied onto a purified PVC plate having a size of 7×10 cm, the distribution and spreading capacity were the better, and after drying the formation of stains and rims was the smaller (visual estimination), the lower the surface tension value of the emulsion used was (see Table 2).

EXAMPLE 16

For the application of biocides, spray powders are used in practice. These powders must have a good floating capacity in water with short wetting times and low foam values. As dispersants are used commercial long-chain alkylphenol-formaldehyde-condensation products. By addition of 0.15% of the substances according to the invention the wetting capacity of the powders is considerably improved without the floating capacity (D) being reduced and the foam values (S) being increased (Table 3).

In comparative tests the floating capacity was determined according to the cyclinder method of Fischer (see "Handbuch der landwirtschaftlichen Versuchs- und Untersuchungsmethodik" (Methodenbuch) Volume VII "Die Untersuchungen von Pflanzenschutzmittein" von W. Fischer (1941) page 53 and page 12, corresponding to the WHO method described in Specifications for Pesticides, 1967, pages 76, 77, 80 and 81 (Column D in Table).

The wetting capacity was determined as follows: A 500 ml beaker (diameter of 8 cm) was filled with tap water of 20° C. and 12° dH (German degree of hardness), and one gram of the spray powder to be tested was sprayed onto the surface. The time required in order to wet the powder was measured and indicated in seconds as wetting time (column N in Table).

The examination of the foaming capacity was carried out according to J. Ross and G. D. Miles (see Oil and Soap 18 (1941), 99): 4 grams per liter of the spray powders to be tested were introduced into water. In each case the height of the foam after shaking was measured in cm in the beginning and after a dwelling time of 5 minutes (column S in Table).

For the comparative tests with the wetting agents and dispersants to be tested the following spray powder compositions were used.

| | | |
|---|---|---|
| A. | 50 Parts of | τ-hexachloro-cyclohexane |
| | 47 Parts | siliceous silicous chalk |
| | 2.85 Parts of | dispersing agent (cresol - formaldehyde - reaction product)* |
| | 0.15 Parts of | test product |
| B. | 50 Parts of | bis-(p-chlorophenyl)-trichloro-ethanol |
| | 10 Parts of | silicic acid |
| | 36 Parts of | siliceous chalk |
| | 3.80 Parts of | dispersing agent (see above) |
| | 0.20 Part of | test product |
| C. | 30 Parts of | hexachloro-endomethylene-bicyclo-heptene(oxymethylene-sulfite) |
| | 3 Parts of | silica |
| | 64 Parts of | siliceous chalk |
| | 2.85 Parts of | dispersing agent (see above) |
| | 0.15 Part of | test product |
| D. | 50 Parts of | trichloromethyl-thiophthalimide |
| | 47 Parts of | siliceous chalk |
| | 2.85 Parts of | dispersing agent (see above) |
| | 0.15 Part of | test product |

*according to German Offenlegungsschrift No. 1,945,100, Example 3 (consisting of 80% of the condensation product of 1 mol of cresol, 0.025 mol of nonyl phenol, 1.78 mols of formaldehyde and 0.75 mol of sodium sulfite; residual 20%: sodium sulfate and water).

TABLE 1

Surface tension values (dyn/cm) of the novel substances in aqueous solution

Substance ROOCCH$_2$CH(SO$_3$Na)COOR'
R= R$_f$CH$_2$CH$_2$(OCH$_2$CH$_2$)$_n$

| No. | R$_f$ | n | R' | \multicolumn{4}{c}{Concentration} |
|---|---|---|---|---|---|---|---|
| | | | | 1.0 | 0.3 | 0.1 | 0.03 |
| 1 | C$_2$F$_5$ | 0 | R | 40.5 | 44.0 | 48.5 | 52.0 |
| 2 | C$_4$F$_9$ | 0 | R | 19.5 | 25.0 | 37.0 | 49.0 |
| 3 | C$_6$F$_{13}$ | 0 | R | 20.0 | 22.0 | 28.0 | 38.0 |
| 4 | C$_8$F$_{17}$ | 0 | R | 26.5 | 30.0 | 37.0 | 41.0 |
| 5 | C$_4$F$_9$ | 1 | R | 19.0 | 22.0 | 27.0 | 41.0 |
| 6 | C$_4$F$_9$ | 2 | R | 20.0 | 22.5 | 28.0 | 43.5 |
| 7 | C$_4$F$_9$ | 3 | R | 21.0 | 23.0 | 29.0 | 46.5 |
| 8 | C$_6$F$_{13}$ | 2 | R | 20.0 | 21.0 | 25.0 | 29.0 |
| 9 | C$_4$F$_9$ | 0 | Na | 18.0 24.0 | 31.0 | 41.0 | |
| 10 | C$_6$F$_{13}$ | 0 | Na | 18.0 | 23.0 | 29.0 | 40.5 |
| 11 | C$_8$F$_{17}$ | 0 | Na | 24.0 | 26.0 | 30.0 | 43.0 |
| 12 | C$_4$F$_9$ | 1 | Na | 18.5 | 23.0 | 30.5 | 40.5 |
| 13 | C$_4$F$_9$ | 3 | Na | 21.0 | 24.0 | 32.0 | 40.0 |
| 14 | C$_6$F$_{13}$ | 2 | Na | 22.5 | 27.0 | 33.5 | 42.5 |

TABLE 2

Surface tension values in wax emulsions according to Examples 14 and 15

| | Product ROOCCH$_2$CH(SO$_3$Na)COOR' R = R$_f$CH$_2$CH$_2$(OCH$_2$CH$_2$)$_n$ | | | surface tension (dyn/cm) acc. to Ex. 14 with addition of | | acc. to Ex. 15 with addition of | |
|---|---|---|---|---|---|---|---|
| No. | R$_f$ | n | R' | 200 ppm | 500 ppm | 200 ppm | 500 ppm |
| 1 | C$_2$F$_5$ | 0 | R | 38.5 | 38.0 | 36.5 | 36.5 |
| 2 | C$_4$F$_9$ | 0 | R | 31.5 | 27.0 | 32.0 | 27.0 |
| 3 | C$_6$F$_{13}$ | 0 | R | 29.0 | 21.5 | 29.5 | 21.0 |
| 4 | C$_8$F$_{17}$ | 0 | R | 39.0 | 38.0 | 35.5 | 35.0 |
| 5 | C$_4$F$_9$ | 1 | R | 32.0 | 27.5 | 32.5 | 28.0 |
| 6 | C$_4$F$_9$ | 2 | R | 32.5 | 28.0 | 32.5 | 28.0 |
| 7 | C$_4$F$_9$ | 3 | R | 33.5 | 29.0 | 33.5 | 30.5 |
| 8 | C$_6$F$_{13}$ | 2 | R | 25.5 | 21.5 | 25.5 | 21.5 |
| 9 | C$_4$F$_9$ | 0 | Na | 34.0 | 30.0 | 34.0 | 30.0 |
| 10 | C$_6$F$_{13}$ | 0 | Na | 27.0 | 20.0 | 27.0 | 20.0 |
| 11 | C$_8$F$_{17}$ | 0 | Na | 39.0 | 38.5 | 35.0 | 36.0 |
| 12 | C$_4$F$_9$ | 1 | Na | 35.5 | 30.5 | 35.0 | 31.0 |
| 13 | C$_4$F$_9$ | 3 | Na | 36.0 | 32.0 | 35.5 | 32.0 |
| 14 | C$_6$F$_{13}$ | 2 | Na | 27.5 | 21.5 | 26.5 | 23.0 |
| 15 | 1/5 C$_4$F$_9$; 4/5 C$_6$F$_{13}$ | 0 | Na | 31.0 | 23.5; | 32.0 | 23.0 |
| 16 | 1/5 C$_4$F$_9$; 4/5 C$_6$F$_{13}$ | 0 | R | 29.5 | 25.0 | 30.0 | 25.0 |
| 17 | 1/5 C$_4$F$_9$; 4/5 C$_6$F$_{13}$ | 0 | 1/2R;1/2Na | 29.5 | 23.5 | 31.0 | 23.5 |
| Comparison: without addition | | | | 41.5 | — | 38.5 | — |

TABLE 3

Application in biocide spray powders
Floating capacity (D), foam (S) and wotting (N) values at a 0.15% addition of the novel substances

| ROOCCH$_2$CH(SO$_3$Na)COOR' R = R$_f$CH$_2$CH$_2$(OCH$_2$CH$_2$)$_n$ | | | | composition A | | | B | | | C | | | D | | | |
|---|---|---|---|---|---|---|---|---|---|---|---|---|---|---|---|---|
| No. | R$_f$ | n | R | D | S | N | D | S | N | D | S | N | D | S | N | H |
| without addition | | | | 87 | 1.0/0.5 | >300 | 57 | 0 | ~300 | 73 | 0 | 140 | 77 | 1,0/0,5 | >300 | |
| 2 | C$_4$F$_9$ | 0 | R | 92 | 2.0/1.5 | 25 | 77 | 2.0/1.0 | 120 | 79 | 2.0/1.0 | 25 | 83 | 2.0/1.0 | 120 | |
| 5 | C$_4$F$_9$ | 1 | R | 30 | 2.5/1.0 | 60 | 34 | 2.0/1.0 | 180 | 82 | 2.5/1.0 | 40 | 81 | 2.0/1.0 | 115 | |
| 6 | C$_4$F$_9$ | 2 | R | 93 | 2.5/1.5 | 45 | 79 | 2.0/1.0 | 180 | 83 | 2.0/0.5 | 35 | 81 | 2.0/0.5 | 55 | |
| 7 | C$_4$F$_9$ | 3 | R | 87 | 2.5/1.5 | 35 | 83 | 2.0/0.5 | 120 | 84 | 2.0/0.5 | 35 | 81 | 2.5/1.0 | 60 | |
| 12 | C$_4$F$_9$ | 1 | Na | 91 | 2.5/1.0 | 50 | 81 | 2.5/1.0 | 240 | 83 | 2.0/1.0 | 35 | 82 | 2.0/0.5 | 120 | |
| 13 | C$_4$F$_9$ | 3 | Na | 91 | 2.5/1.5 | 30 | 83 | 2.5/1.5 | 170 | 83 | 2.0/1.0 | 35 | 81 | 2.5/0.5 | 55 | |
| 3 | C$_6$F$_{13}$ | 0 | R | 30 | 2.5/1.0 | 25 | 75 | 2.0/1.0 | 130 | 79 | 2.0/1.0 | 25 | 82 | 2.0/1.0 | 130 | |
| 18 | C$_6$F$_{13}$ | 2 | R | 91 | 2.5/1.5 | 50 | 80 | 2.0/1.0 | 195 | 82 | 2.0/1.0 | 40 | 82 | 2.0/0.5 | 60 | |

We claim:

1. A compound of the formula $$R-O-CO-CH_2-CH(SO_3M)-CO-O-R^1$$

in which R is a group of the formula $$R_f-(CH_2)_m-OCH_2CH_2)_n$$

wherein $R_f$ is straight-chain or terminally methyl-branched perfluoroalkyl of 2 to 8 carbon atoms, m is a number of 1 to 4, n is a number of zero to 3, M is hydrogen, an alkali metal, ammonium, monoethanolammonium, diethanolammonium, triethanolammonium, glycinium, taurinium, and N-methyltaurinium, and $R^1$ is defined as R or as M.

2. A compound as defined in claim 1, wherein $R_f$ is n-perfluoroalkyl.

3. A compound as defined in claim 1, wherein $R_f$ is n-perfluoroalkyl of 4 to 6 carbon atoms.

4. A compound as defined in claim 1, wherein m is 1, 2 or 4.

5. A compound as defined in claim 1, wherein m is 2.

6. A compound as defined in claim 1, wherein M is sodium or potassium.

7. The compound as defined in claim 1, wherein $R_f$ is n-C$_6$F$_{13}$, n is 2, m is 2, M is sodium and $R^1$ is as R.

8. The compound as defined in claim 1, wherein $R_f$ is n-C$_6$F$_{13}$, m is 2, n is zero, M is sodium and $R^1$ is as R.

9. The compound as defined in claim 1, wherein $R_f$ is n-C$_6$F$_{13}$, m is 2, n is zero and M and $R^1$ are sodium.

10. The compound as defined in claim 1, wherein $R_f$ is n-C$_6$F$_{13}$, m is 2, n is 2 and M and $R^1$ are sodium.